United States Patent [19]

Fujita et al.

[11] 4,070,284
[45] Jan. 24, 1978

[54] LIQUID CHROMATOGRAPHY AND APPARATUS FOR THE SAME

[75] Inventors: Kazunori Fujita, Ibaraki; Seiji Takeuchi, Hitachi; Yoshinori Takata, Ibaraki; Mamoru Taki, Hitachi; Yoshimasa Hamano, Katsuta, all of Japan

[73] Assignee: Hitachi, Ltd., Japan

[21] Appl. No.: 673,529

[22] Filed: Apr. 5, 1976

Related U.S. Application Data

[63] Continuation of Ser. No. 496,829, Aug. 12, 1974, abandoned.

[30] Foreign Application Priority Data

Aug. 20, 1973 Japan .................................. 48-92490

[51] Int. Cl.$^2$ .......................................... B01D 15/08
[52] U.S. Cl. .............................. 210/31 C; 210/198 C
[58] Field of Search ................ 55/67, 197, 386, 513, 55/512; 210/31 C, 198 C, 282, 232, 234, 235

[56] References Cited

U.S. PATENT DOCUMENTS

| | | | |
|---|---|---|---|
| 3,250,395 | 5/1966 | Blume | 55/386 X |
| 3,440,864 | 4/1969 | Blume | 210/198 C |
| 3,686,117 | 8/1972 | Lauer et al. | 210/31 C |
| 3,790,348 | 2/1974 | Bossart | 55/386 X |
| 3,855,130 | 12/1974 | Randau et al. | 210/198 C |
| 3,897,213 | 7/1975 | Stevens et al. | 210/31 C |
| 3,926,559 | 12/1975 | Stevens | 210/31 C |
| 3,926,589 | 12/1975 | Klementi et al. | 55/197 X |

Primary Examiner—John Adee
Attorney, Agent, or Firm—Craig & Antonelli

[57] ABSTRACT

A definite, but large amount of a sample solution is fed to a small concentration column filled with a packing material to retain in the concentration column components to be measured in the sample solution. Then, a small amount of a desorbing solution is fed to the concentration column to desorb the components retained in the concentration column. The effluent solution containing the desorbed components is fed to a separation column filled with a packing material. An eluting solution is fed to the separation column to separate the components from one another, and the components are detected by a detector.

Since the components are separated from one another after their concentrations have been elevated, and thus the components can be measured with a high sensitivity.

36 Claims, 10 Drawing Figures

LIQUID CHROMATOGRAPHY AND APPARATUS FOR THE SAME

This is a continuation, of application Ser. No. 496,829 filed Aug. 12, 1974, abandoned.

BACKGROUND OF THE INVENTION

This invention relates to a liquid chromatography in which concentrations of components contained in a solution to be introduced into a separation column are elevated before the introduction of the solution into the separation column, and an apparatus for carrying out the liquid chromatography.

In liquid chromatography, a dilute sample solution containing only a very small amount of components to be measured must be often subjected to the measurement. Therefore, it is an indispensable condition to increase the sensitivity of a detector, but even if a measuring apparatus with the highest sensitivity is used, there still are components at a concentration too low to measure the components. In that case, it is effective to concentrate a sample in advance. According to the conventional procedure, the dilute sample components are concentrated in advance by evaporation or solvent extraction, but these concentrating operations are carried out with equipment or device or special reagents having nothing to do with the apparatus for liquid chromatography. Therefore, there are so many changes for errors of measurement.

Furthermore, the concentration based on the evaporation or solvent extraction generally requires much time, and complicates operations. It takes a few minutes to several tens of minutes in the chromatographic separation and detection according to an apparatus for liquid chromatography, but it takes much more time in the concentration as a pretreatment for the chromatography than in the chromatographic separation and detection. Thus, the feature or capacity of the apparatus for liquid chromatography cannot be fully attained. Furthermore, the evaporation and solvent extraction require much labor.

In the measurement, it should be taken into consideration that, as soon as a solution containing components to be measured reaches a separation column, the separation starts to take place. When a large amount of a solution must be introduced into the separation column, that is, it takes much time in the introduction into the separation column, it will be difficult to separate the components from one another. Therefore, it must be avoided to introduce a large amount of the solution to the separation column.

SUMMARY OF THE INVENTION

An object of the present invention is to provide a liquid chromatography, capable of efficiently concentrating dilute sample components and measuring these components with a high sensitivity, and an apparatus for carrying out the liquid chromatography.

Another object of the present invention is to provide a liquid chromatography capable of carrying out concentration of dilute sample components, and separation of these components from one another simply in one and same apparatus for liquid chromatography resulting in reduction in complicated operations, and an apparatus for carrying out the liquid chromatography.

Other object of the present invention is to provide a liquid chromatography, which comprises simply effecting sampling and concentration at a site for sample collecting by means of a structural part of an apparatus for liquid chromatography, and placing the structural part holding sample components in the apparatus for liquid chromatography, thereby effecting measurement of the sample components, and an apparatus for carrying out the liquid chromatography.

Further objects of the present invention will be apparent from the disclosure of the desirable embodiments of the present invention, which follow.

The present invention is characterized by elevating a concentration of components to be measured, which are contained in a definite amount of a sample solution, by means of a concentration column, then separating the components from one another in a separation column, and detecting the separated components.

DETAILED DESCRIPTION OF THE PREFERRED EMBODIMENT

In the present invention, a concentration of substances contained in a sample solution is elevated by means of a column filled with a packing material before separating components to be detected to one another.

According to one of methods for concentrating components to be measured in a sample solution by means of a packed column, the concentration is carried out in an upper part of the column and chromatographic separation is carried out in the lower part of the same column. That is, these two operations are carried out in one column. This one-column method has advantages in the shortening of the time and operability, as compared with a combination of the concentration method and the chromatographic separation to be carried out individually. However, in the one-column method, wherein the concentration and chromatographic separation are carried out at the same time, it is difficult to obtain a high precision in the measurement of the individual components. Components in a sample solution must be held within a narrow band in the column in the case of concentration, and must be so developed to provide a good separation between the individual components, but this is rather difficult to attain in one column. The measurement of the components in a dilute solution involves a step of concentration and a step of separation of the components into one another, and it is necessary to wash the column before as well as after the concentration. In the case the concentration and separation are carried out in one column, the effect of the amounts of the solvent of the sample solution and the washing solution remaining in the column are not negligible. Furthermore, there is less advantage with respect to time, because concentration and separation are carried out for another sample after the concentration step and separation step have been completed for one sample.

In the present invention, the step of concentration and the step of separation of the components into one another are carried out in their individual columns, whereby the concentration and separation can be carried out in parallel. Furthermore, the amounts of the solvent of the sample solution and the washing solution can be made smaller thereby, and thus a large Signal-to-Noise Ratio (SN ratio) can be obtained. Further, both ionic and non-ionic substances can be measured with a high precision.

Furthermore, according to the present invention, a sample can be readily transported in sampling by using a detachable concentration column, and the small concentration column, in which the components of the dilute sample solution are accumulated, is connected to a separation column to effect the measurement in a short time with a good accuracy.

Several embodiments of the present invention will be explained, referring to the accompanying drawings.

Figure 1:
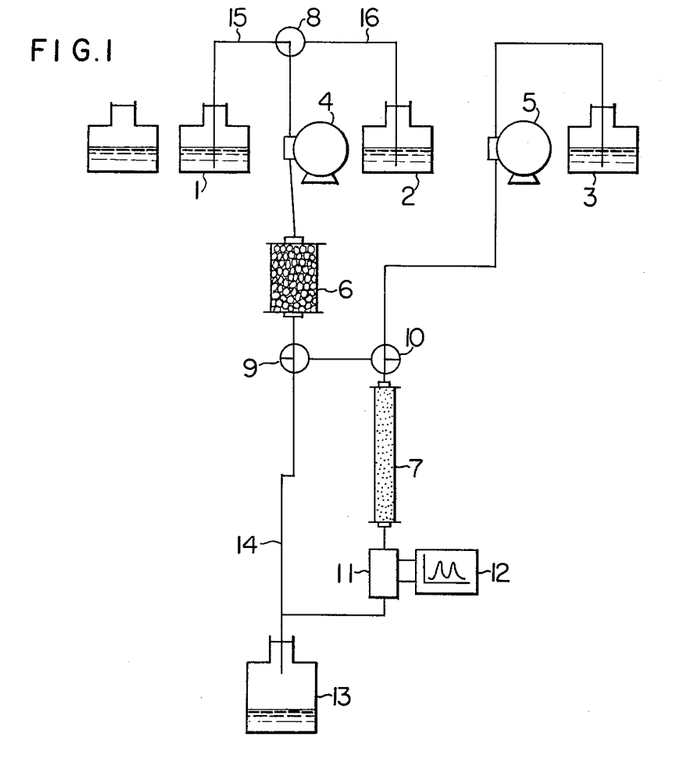
FIG. 1 is a diagram showing an outline structure of one embodiment according to the present invention.

In FIG. 1, where an outline structure of one embodiment of the present invention is illustrated, numeral 6 is a concentration column packed with a suitable packing material for retaining components in a narrow band therein. Numeral 7 is a separation column packed with a suitable packing material for separating the components into one another. Numeral 1 is a sample solution tank containing one of sample solutions to be measured, and the tank 1 is connected to a threeway valve 8 through a conduit 15. Numeral 2 is a desorbing solution tank containing a desorbing solution capable of desorbing the components retained in the concentration column 6, and the tank 2 is connected to the three-way valve 8 through a conduit 16. The threeway valve 8 is connected to the concentration column 6 through a feed pump 4. Numeral 3 is an eluting solution tank containing an eluting solution to be used for separating the components from one another, and the tank 3 is connected to the separation column through a feed pump 5 and a three-way valve 10. Numeral 9 is a three-way valve provided between the concentration column 6 and the three-way valve 10 and the conduit connected to the three-way valve 9 is inserted into a waste liquor tank 13. Numeral 11 is a detector comprising an ultraviolet photometer, coulometrical detector, etc., and the detector 11 is electrically connected to a recorder 12.

In the embodiment of such a structure as described above, the feed pumps are actuated in relation to the three-way valves. The feed pump 4 can be continuously actuated, whereas the pump 5 can be intermittently actuated. When the pump 5 is actuated, the three-way valve 10 is switched to communicate the pump 5 with the separation column 7, and the communicated state can be maintained.

In the first state, the sample solution is led to the concentration column 6. In that state, the threeway valve is swiched to communicate the conduit 15 with the pump 4, and at the same time the three-way valve 9 is switched to communicate the concentration column 6 with the conduit 14. The pump 5 is actuated, and at the same time the three-way valve 10 is switched to communicate the pump 5 with the separation column 7 to feed the eluting solution to the separation colum 7 for a proper, but definite period of time, while such state is maintained.

In the second state, the desorbing solution is sent to the concentration column 6. In that state, the three-way valve 8 is switched to communicate the conduit 16 with the pump 4. At the same time the valve 9 is switched to communicate the concentration column 16 with the three-way valve 10, and further the valve 10 is switched to communicate the valve 9 with the separation column 7.

Switching of these valves can be carried out by the ordinary change-over time switch. A change-over cycle of the valves is selected in accordance with a degree of concentration of a dilute sample solution. The volume of the sample solution to be fed to the concentration columb 6 is larger than the volume of the desorbing solution to be successively fed thereto, and a ratio of these volumes represents the degree of concentration. Therefore, the time for communication of the valve 8 with the conduit 15 is considerably longer than the time for communication of the valve 8 with the conduit 16.

According to this embodiment, operation starts, first of all, by continuously feeding the first sample solution to the concentration column 6 and discharging it into the waste solution tank 13. During that operation, components contained in the sample solution are retained and accumulated in the concentration column 6. Then, the valves 8, 9 and 10 are switched to feed the necessary amount of the desorbing solution for desorbing the components, which are accumulated in the concentration column 6, to the concentration column 6. The components desorbed from the concentration column 6 are led to the separation column 7 together with the effluent desorbing solution. Then, the valves 8, 9 and 10 are switched to feed the eluting solution to the separation column by the pump 5. At the same time, the second sample solution is fed to the concentration column 6, since the conduit 15 is communicated with the second sample solution tank. The components are accumulated in the concentration column 6. The effluent containing components separated from one another in the separation column 7 reaches the detector 11, where the components are detected, and a chromatogram based on these components is described on the recorder 12. The measured solution is discharged into the waste solution tank 13. Generally, the period for feeding the sample solution to the concentration column 6 is longer than the period for feeding the eluting solution to the separation column 7, and therefore the separation of the components from one another and the detection of the components, which are contained in the first sample solution are completed, while the components coming from the second sample solution are accumulated in the concentration column 6.

The concentration column 6 is made as small as possible, so that the time for feeding the components retained in the concentration column 6 may be rendered shorter.

In the case the concentration column 6 is small, an extension of a band of the components retained therein will be also smaller. The size of the concentration column used in this embodiment is 0.2 to 0.4 inches in diameter and 0.2 to 0.6 inches in length, but the size is not limited to these figures. In the case of such a small column, the dead volume will be smaller, and the effect by the dead volume will be also less. In FIG. 1, two feed pumps are used, but only one pump can serve the purpose by increasing the number of switch valves. Further, it is possible to wash the inside of the column at the concentration.

To efficiently carry out the concentration, and separation followed by detection in practice of the embodiment, selection of the kind of a packing material for the concentration column, composition of a desorbing solution, kind of a packing material for the separation column, and composition of an eluting solution for the separation, etc. is important.

When a sample solution containing non-ionic substances is concentrated, separated and detected, it is possible to use an organic porous adsorbent consisting of styrene-divinylbenzene copolymer, etc., or active carbon as the packing material for the concentration column and the separation column. It is preferable that the particle size of the packing material for the concentration column is larger than that of the packing material for the separation column. The organic porous adsorbent, for example, commercially available XAD-2 or XAD-4, (a trade mark of products made by Rohm and Haas Company) can adsorb non-ionic substances very well in a solvent having a high polarity such as an aqueous solution, and therefore the components coming from the sample solution can be kept in a narrow band in the concentration column packed with such an organic porous adsorbent. The components held in such a concentration column can be desorbed by a solvent having a low polarity. Ethyl ether, n-hexane, isopropyl alcohol, an aqueous solution containing lithium chloride and methanol, etc. can be used as the desorbing solution. To measure the non-ionic substance, a different kind of the desorbing solution from an eluting solution is usually used. Methanol, a mixed solution of n-hexane and methanol, a mixed solution of water and methanol, etc. can be used as the eluting solution.

Figure 2:
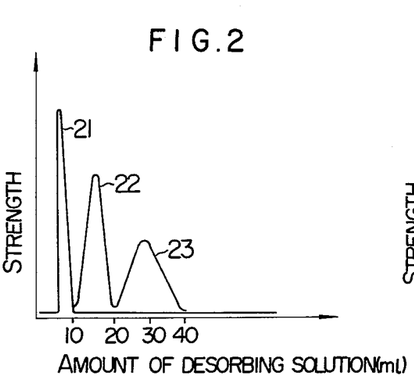
FIG. 2 is a diagram showing comparison of the amount and kind of desorbing solutions necessary for desorbing parathion accumulated in a concentration column.

In FIG. 2, the amounts of the desorbing solution necessary for desorbing parathion retained in the concentration column are compared with the kinds of the desorbing solution, where porous styrene-divinylbenzene copolymers are filled in the concentration column, and three desorbing solutions, that is, ethyl ether, a mixed solution of normal hexane and methanol, and methanol, are used. To a concentration column is fed 500 ml of an aqueous solution containing 1 ppm of parathion, pesticide of organic phosphorus compound, at a flow rate of 4 ml/min., and the quantitative desorption state of parathion in an effluent solution from the concentration column is continuously measured by an ultra-violet photometer. From the forms of the individual peaks in FIG. 2, the necessary amounts and strength of the desorbing solutions are known, when ethyl ether 21, a mixed solution 22 of n-hexane and methanol, and methanol 23 are used as the desorbing solutions, individually. To completely desorb parathion, 10 ml of ethyl ether, 20 ml of the mixed solution of n-hexane and methanol, and 40 ml of methanol are required, individually. It is seen from the foregoing fact that, when a solvent having a low polarity is used as the desorbing solution, a smaller amount of the desorbing solution can meet the necessary desorption. To obtain a higher degree of concentration and an excellent measurement result, it can be seen that a solvent having a lower polarity is more preferable. The solvents having a small polarity include, for example, ethyl ether, tetrahydrofuran, isopropyl ether, methylene chloride, acetic acid, dioxane, etc.

Figure 3:
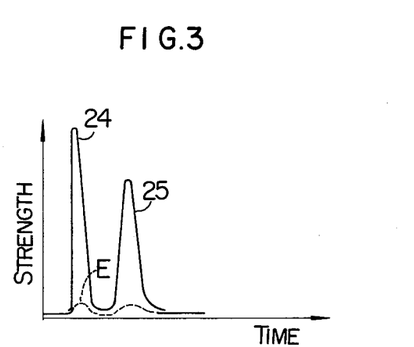
FIG. 3 is a chromatogram showing measurement examples of a mixed solution of benzene and naphthalene.

Now, examples of measuring the non-ionic substance will be described below:

1. Porous styrene-divinylbenzene copolymers are filled in both concentration column and separation column, and ethyl ether is used as a desorbing solution, while a mixed solution of n-hexane and methanol is used s an eluting solution. To the concentration column is fed 200 ml of an aqueous solution containing 1 ppm each of benzene and naphthalene to accumulate benzene and naphthalene therein. Then, the accumulated benzene and naphthalene are desorbed by 20 ml of ethyl ether, and separated in the 20-inch long separation column, and detected by an ultra-violet photometer. Chromatograms of benzene 24 and naphthalene 25 concentrated 10 times the original concentration in this manner is shown in FIG. 3. E in FIG. 3 is a chromatogram when measured without concentration. The time required for the concentration and detection of the first sample solution is about one hour, and the time required for the second and successive measurements can be shortened by an overlapping of the concentration and the separation-detection.

2. A concentration column filled with active carbon and a separation column filled with styrenedivinylbenzene copolymers are used. Isopropyl alcohol is used as a desorbing solution, whereas methanol is used as an eluting solution. A sample solution containing an ABS surface-active agent is measured.

3. Styrene-divinylbenzene copolymers are filled in both concentration column and separation column. An aqueous solution containing lithium chloride and methanol is used as a desorbing solution, whereas methanol is used as an eluting solution. A sample solution containing phenol is measured.

Figure 4:
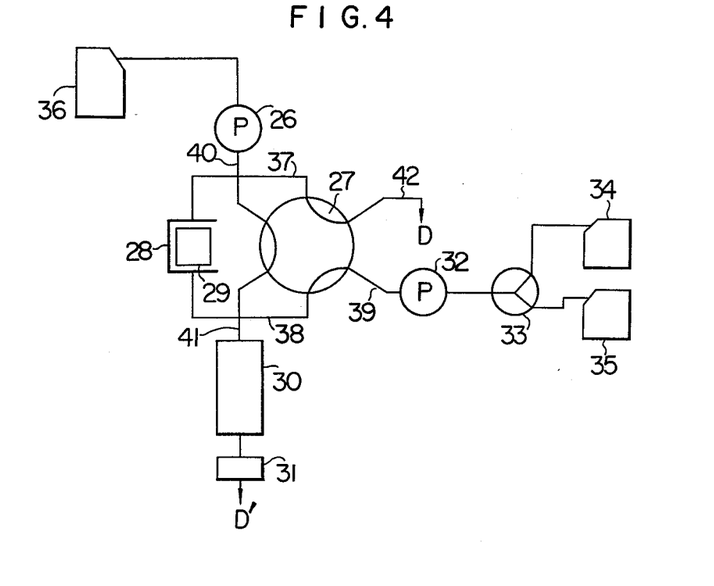
FIG. 4 is a diagram showing an outline structure of another embodiment according to the present invention.

When the components to be measured have an ionic property, the same solution can be used as both desorbing solution and eluting solution. In FIG. 4, one embodiment of an apparatus for liquid chromatography, which is comprised for the measurement of such a sample solution, is shown. In FIG. 4, an eluting solution contained in an eluting solution tank 36 is fed to a concentration column 29 or a separation column 30 by a feed pump 26. A sample solution tank 34 containing a sample solution containing ionic components and a washing liquid tank 35 containing a washing liquid comprising distilled water, etc. are connected to a switch valve 33, and the switch valve 33 is connected to a feed pump 32. A concentration column 29 is inserted in a column holder 28 in a detachable manner, for example, in a plug type, and exchangeable. In the concentration column 29, ion exchange resin or chelate resin having relatively large particle sizes is filled. In a separation column 30, ion exchange resin or chelate resin having small particle sizes is filled. A detector 31 consisting of a coulometric monitor, etc. is connected to the separation column 30. The column holder 28 are connected to a six-way switch valve 27 through conduits 37 and 38. The six-way swich valve 27 is a valve of fitting type, made from fluorine resin, and the parts represented by arcs in FIG. 4 are passages. The feed pump 32 is connected to the six-way switch valve 27 through a conduit 39. A conduit 40 is connected to the feed pump 26 and the switch valve 27, and the conduit 41 is connected to the switch valve 27 and the separation column 30. A conduit 42 is connected to a waste solution tank (not shown in the drawing). Change-over sequence of the switch valves 27 and 33, and driving sequence of the feed pumps 26 and 32 are selected by a change-over time switch (not shown in the drawing).

Measurement operation consists of 5 steps. The first step is a step for washing the inside of the concentration column 29. While the switch valve 33 is brought in such a state as to communicate the washing liquid tank 35 with the pump 32, the six-way switch valve is switched from other state to the state shown in FIG. 4, that is, such a state as to communicate the conduit 38 with the conduit 39, the conduit 37 with the conduit 42, and the conduit 40 with the conduit 41, individually. The washing liquid is fed to the concentration column 29 by the pump 32, and discharged through the conduit 42 after washing the inside of column 29.

The second step is a step for accumulating the components contained in the sample solution within the concentration column 29. The six-way switch valve 27 is kept in the same state as in the first step, while the switch valve 33 is switched into such a state as to communicate the sample solution tank 34 with the pump 32. The sample solution is continuously fed to the concentration column 29 by the pump 32, and discharged through the conduit 42. The volume of the sample solution to be fed is determined by flow rate and time. During that feeding, the components contained in the sample solution are retained, and accumulated within the concentration column 29.

The third step is a step for washing the inside of the concentration column 29 retaining the components. While the six-way switch valve 27 is kept in the same state as above, the switch valve 33 is switched to such a state as to communicate the washing liquid tank 35 with the pump 32. The washing time is considerably shorter than the accumulation time of the second step.

The fourth step is a step for leading the components accumulated in the concentration column 29 to the separation column 30. While the switch valve 33 is kept in the same state as in the third step, the sixway switch valve 27 is switched, so that it may be turned by 60° from the state shown in FIG. 4. The conduit 37 is communicated with the conduit 40, the conduit 38 with the conduit 41, and the conduit 39 with the conduit 41, thereby individually. The eluting solution is fed to the concentration column 29 from the eluting solution tank 36 by the pump 26, and the accumulated components are desorbed thereby and led to the separation column 30 through the switch valve 27.

The fifth step is a step for separating the components, which are intoduced into the separation column, into one another, and detecting the separated components. While the switch valve 33 is kept in the same state as in the fourth step, the six-way switch valve 27 is switched to the state as shown in FIG. 4, that is, so as to communicate the conduit 40 with the conduit 41. The eluting solution is fed to the separation column 30 without any passage through the concentration column 29.

The state of the six-way valve 27 in the fifth step is the same as in the first, second and third steps. Therefore, while the components of the next sample solution are treated in the first to third steps, the separation and detection of the components of the preceding sample solution are carried out in the fifth step. It is possible to exchange the concentration column 29 before the first step is carried out again. Since the necessary time for the fifth step is generally less than the necessary time for the second step, the fifth step for the preceding sample can be completed while the first and second steps are carried out for the next sample.

Figures 5, 6:
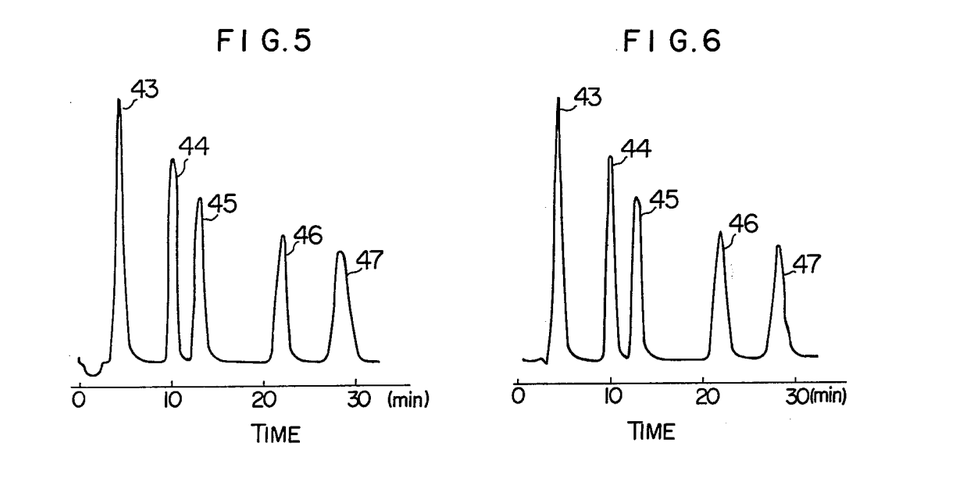
FIG. 5 is a diagram showing measurement results of a sample solution containing metallic ions.
FIG. 6 is a diagram showing measurement results of a solution having a concentration, which is 200 times as dillute as the solution used in reference to FIG. 5, without any concentration.

An example of concentrating, and separating and detecting a sample solution containing ionic substances will be given below:

FIG. 5 is a chromatogram showing a measurement result of a sample solution containing metallic ions according to the present invention, and FIG. 6 is a chromatogram of a measurement result of a solution having a component solution, which is 200 times the concentration of the solution used in reference to FIG. 5, without any concentration. The concentration column used for obtaining the chromatogram of FIG. 5 is 0.24 inches in inner diameter, and 0.4 inches in length, and the separation column is 0.36 inches in inner diameter and 4 inches in length. The packing materials for both concentration column and separation column are the same cation exchange resin. The desorbing solution and the eluting solution are identical with each other, that is, an ammonium tartrate solution of 0.2 molar concentration (pH 4.6). The detector is a Hitachi coulometric monitor suitable for detecting metallic ions. The sample solution used for obtaining the chromatogram of FIG. 5 contains $Cu^{++}$ 43, $Zn^{++}$ 44, $Ni^{++}$ 45, $Co^{++}$ 46, and $Cd^{++}$ 47, each at $5 \times 10^{-6}$ molar concentrations, and the sample solution used for obtaining the chromatogram of FIG. 6 contains the same metallic ions, each at $10^{-3}$ molar concentrations. Detection can be carried out with equal sensitivity both in the case where the thick sample solution is measured without any concentration, as shown in FIG. 6, and in the case where the dilute sample solution is measured after concentrating the component concentration of the solution to 200 times the original concentration, as shown in FIG. 5. Thus, it is seen that the present invention is effective upon the measurement of a dilute sample solution.

The following Table illustrates column packing materials and eluting solutions suitable for measuring sample solutions containing various ionic components.

| Sample and component | Packing materials for concentration | Packing materials for separation | Desorbing solution and eluting solution |
| --- | --- | --- | --- |
| Metallic ions in river water ($Zn^{2+}$, $Na^{2+}$, $Pb^{2+}$, $Co^{2+}$, $Cu^{2+}$, $Cd^{2+}$, $Hg^{2+}$) | Cation exchange resin | Cation exchange resin | Aqueous solution of sodium tartrate |
| Metallic ions in water (same seven components as above) | Cation exchange resin | Cation exchange resin | Aqueous solution of sodium lactate |
| Metallic ions in sea water ($Cd^{2+}$, $Hg^{2+}$) | Anion exchange resin | Cation exchange resin | Aqueous solution of sodium tartrate |
| Halogen ions in water ($Br^-$, $I^-$) | Anion exchange resin | Anion exchange resin | Aqueous solution of sodium nitrate and acetone |
| Chromium (VI) ion in water | Anion exchange | Anion exchange | Aqueous solution of sodium |

| Sample and component | Packing materials for concentration | Packing materials for separation | Desorbing solution and eluting solution |
|---|---|---|---|
| | resin | resin | sulfate |

An apparatus for liquid chromatography according to the present invention can comprise a small concentration column capable of accumulating components of a sample solution in advance, the concentration column being inserted in a passage of a desorbing solution in a detachable manner. In that case, a mechanism for feeding the sample solution to the concentration column will not be required. The desorbing operation, and separating-detecting operation are carried out by the apparatus for liquid chromatography, and an operation to accumulate the components of the sample solution in the concentration column is carried out at another place, using the concentration column, which is detachable from the apparatus for liquid chromatography.

A large number of large containers containing a large amount of sample solution or water must be transported to a laboratory from a sample-collecting site, when river water, sea water, etc. are analyzed.

The small concentration column used in the embodiment of the present invention is simply detachable from the apparatus for liquid chromatography, and can be readily transported without much labor. At the sample-collecting site, a very small amount of the components contained in much sample solution or water can be retained in the small concentration column by connecting the concentration column to an injection device, etc., or allowing the sample solution or water to flow through the concentration column by gravity, for example, by head difference.

Figure 7:
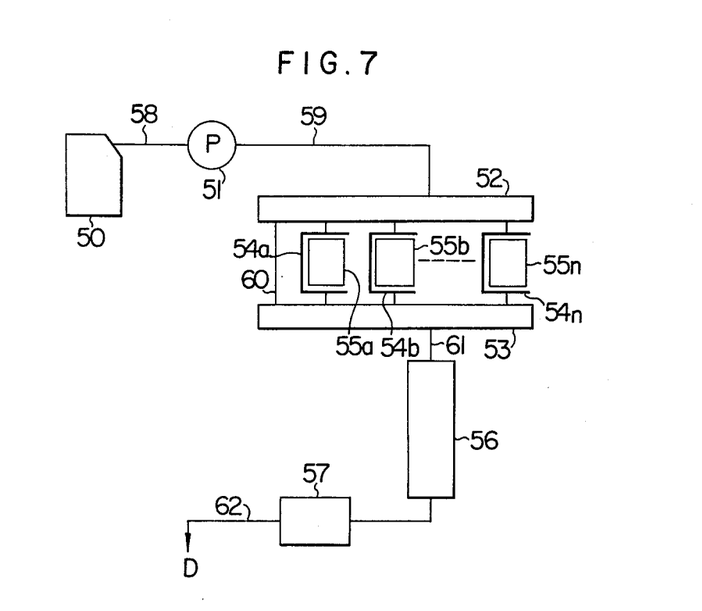
FIG. 7 is a diagram showing an outline structure of other embodiment according to the present invention.

FIG. 7 shows an outline structure of one embodiment of the present invention, provided with the detachable concentration columns. The structure of the embodiment is directed to the measurement of a sample solution containing ionic substances, and the same solution is used as both desorbing solution and eluting solution. An eluting solution tank 50 is connected to a feed pump 51 through a conduit 58, and the feed pump 51 is connected to a multi-way switch valve 52 through a conduit 59. The multi-way switch valve 52 used in this embodiment is in the following construction. The multi-way valve is provided with a pair of stators having a circular concave part, and a disc-type rotor placed between these stators. At both sides of the rotor, there are circular convex parts having a size almost equal to that of the concave parts of the stators. The stators and the rotor are arranged so that the concave parts of the stators and the convex parts of the rotor can slide closely face to face. On the surfaces of the convex parts of the rotor, there are provided grooves serving as liquid passages, and on the stators there are a plurality of perforations capable of selecting the passage through the groove. The perforations are connected to the outside tubes. A gear is provided at the outer periphery of the disc-type rotor, and a force is transferred to the gear from a driving device consisting of a rotary solenoid to rotate the rotor. By rotation of the rotor, the passage is switched by selecting the perforation through the groove on the rotor.

A multi-way switch valve 53 is a valve of the same kind as that of the switch valve 52, and these valves 52 and 53 are interlocked with each other. Between the multi-way switch valves 52 and 53, there are provided a conduit 60 and a plurality of column holders 54a, 54b, . . . , 54n, and small concentration columns 55a, 55b, . . . , 55n can be inserted into the corresponding column holders 54a, 54b, . . . , 54n. The switch valve 53 is connected to a separation column 56 through a conduit 61, and the separation column 56 is connected to a detector 57. A conduit 62 serves to discharge the solution leaving the detector 57.

The concentration column 55, in which a very small amount of components contained in a large amount of a sample solution is accumulated at another place, is inserted into the column holder 54. The multi-stage switch valves 52 and 53 are switched in an interlocked manner to communicate the conduit 59 with the column holder 54a, and the column holder 54a with the conduit 61. The eluting solution is fed to the concentration column 55a from the eluting solution tank 50 by the feed pump 51, and the components retained in the concentration column 55a are desorbed, and led to the separation column 56.

Then, the switch valves 52 and 53 are switched to communicate the conduit 59 with the conduit 60, and the conduit 60 with the conduit 61. The eluting solution is fed to the separation column 56 through the conduit 60, and the separation of the components into one another is started. An effluent from the separation column 56, which contains the separated components, is led to the detector 57, where the individual components are detected. After the first measurement has been completed, the switch valves 52 and 53 are switched to communicate the conduit 59 with the column holder 54b, and the column holder 54b with the conduit 61. Desorption and mutual separation of the components are then carried out by the eluting solution in the same manner as described above.

Figure 8:
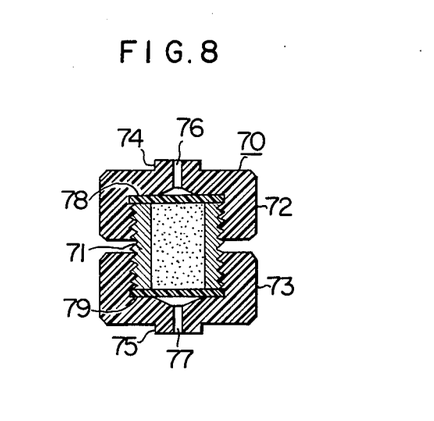
FIG. 8 is a cross-sectional, vertical view of one embodiment of a structure of a detachable concentration column used in one embodiment of the present invention.
Figure 9:
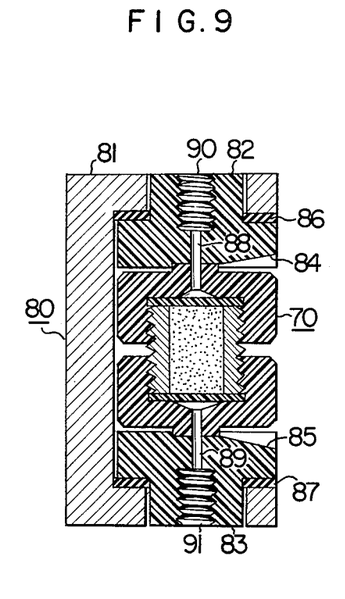
FIG. 9 is a cross-sectional, vertical view of a column holder holding the detachable concentration column of FIG. 8.
Figure 10:
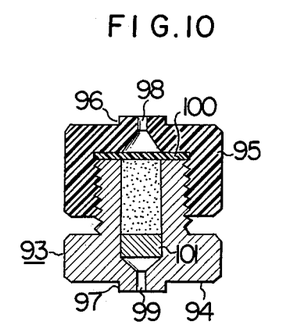
FIG. 10 is a cross-sectional, vertical view of another embodiment of a structure of a concentration column, which is detachable from the column holder of FIG. 9.

FIG. 8 shows a structure of one embodiment of the detachable concentration column, and FIG. 10 shows a structure of another embodiment of the column applicable in the similar manner. FIG. 9 is a crosssectional vertical view of the concentration column of FIG. 8 inserted in the column holder.

In FIG. 8, a concentration column 70 comprises a cylindrical vessel 71, an upper lid 72 and a lower lid 73. The outside wall of the vessel 71 is cut in screw threads, and packing materials are filled in the vessel 71. The upper lid 72 and the lower lid 73 have outwardly-projecting parts 74 and 75, respectively, and liquid passages 76 and 77 are penetrated through the outwardly projecting parts 74 and 75 at their centers, respectively. The inside walls of the upper lid 72 and the lower lid 73 are cut in screw threads, and are engaged with the threaded outer wall of the vessel 71. Filters 78 and 79 consisting of porous fluorine resin are placed on the upper end and the lower end of the vessel 71. Peripheral parts of the filters 78 and 79 are pasted with a rubber paste at their surfaces, and their filtering action is prevented by the rubber sealing. Therefore, the peripheral parts serve to prevent a solution leakage as packings. The central parts of the filters 78 and 79 have the filtering action. If the vessel 71 and the lids 72 and 73 are made from, for example, acrylic resin, a concentration column having a resistance to pressure of 30 kg/cm$^2$ can be obtained.

In a column holder shown in FIG. 9, a concentration column as shown in FIGS. 8 and 10 is inserted. A block 81 supports a pair of connectors 82 and 83, and annular rubber sheets 86 and 87 consisting of silicone rubber are interposed between the block 81 and the connector 82 or 83. These rubber sheets 86 and 87 exert a cushioning action against a pressing force in a vertical direction in the drawing. Connection holes 90 and 91, which are open to outer surfaces of the connectors 82 and 83 placed against each other, are to connect the column holder 80 to outside feed tubes. A liquid passage 88 communicates the outside feed tube to be connected to the connector 82 with the liquid passage 76 of the concentration column 70, and a liquid passage 89 communicates the outside feed tube to be connected to the connector 83 with the liquid passage 77 of the column 70. Taper parts 84 and 85 are provided at open sides of the connectors 82 and 83, respectively.

The concentration column 70 can be inserted into the column holder 80 from the open sides of the column holder 80, that is, the side at which the taper parts 84 and 85 of the connectors 82 and 83 are made open and extended outwardly, so that the projected parts 74 and 75 may be guided by the taper parts 84 and 85. In such a state that the concentration column is inserted in the column holder, a resilience pressure due to the cushioning action of the rubber sheets 86 and 87 exerts upon fitting surfaces each of the upper and lower lids 72 and 73 of the column 70 and the upper and lower connectors 82 and 83, and therefore a tight sealing can be kept therebetween, preventing a liquid leakage.

A concentration column 93 shown in FIG. 10 comprises a vessel 94 filled with the packing materials and a lid 95 screwed to the vessel 94. There are an outwardly-projected part 96 on the lid 95, and an outwardly-projected part 97 on the vessel 94. The lid 95 is provided with a liquid passage 98, and the vessel 94 is also provided with a liquid passage 99. On an upper surface of the vessel 94, there is placed a filter 100, whose peripheral part is sealed with rubber. A filter 101 is provided at the bottom of the packing materials in the container 95 to prevent the packing materials from flowing-out. The concentration column of such a structure can be handled in the same manner as the column of FIG. 8, and can be very readily engaged with or disengaged from the column holder without using any tool, etc. Continuous measurement of the components in a dilute sample solution can be simplified by using these concentration columns.

What is claimed is:

1. A liquid chromatography process comprising feeding a predetermined amount of a sample solution having adsorbable components therein to a concentration column capable of producing a solution of said adsorbable components in higher concentration than the concentration of the adsorbable components in the sample solution to be measured, accumulating said adsorbable components in said concentration column resulting in concentration of said adsorbable components, desorbing the adsorbable components accumulated in said concentration column with a desorbing solution, the amount of desorbing solution being smaller than said predetermined amount of said sample solution, feeding the desorbing solution containing the desorbed components to a separation column, separating the components from one another with an eluting solution fed to said separation column, and detecting the components contained in an effluent from said separation column.

2. The process of claim 1, wherein packing material in said concentration column is an ion exchange resin having a larger particle size than the particle size of the packing materials in said separation column.

3. The process of claim 1, wherein the packing material in said concentration column is a chelate resin having a larger particle size than the particle size of the packing material in said separation column.

4. The process of claim 1, wherein the desorbing solution for desorbing the components accumulated in said concentration column is identical with the eluting solution for separating the components from one another in said separation column.

5. The process of claim 1, wherein said concentration column is filled with an organic porous adsorbent and further wherein said desorbing solution is a solvent having a low polarity.

6. The process of claim 1, wherein a plurality of different samples are to be successively analyzed, the adsorbable components in one of said samples being separated from one another in said separation column while the adsorbable components in another sample are being accumulated in said concentration column.

7. A liquid chromatography process comprising
   a. connecting an outlet of a concentration column to a discharge outlet in an interrupted state of communication of the concentration column with a separation column and feeding a washing solution to the concentration column through a passage switch means,
   b. discharging the washing solution,
   c. feeding a sample solution containing adsorbable components to be measured to said concentration column through said switch means while keeping said switch means and the outlet of the concentration column in the same state as in said step (a),
   d. discharging the solvent of the sample solution flowing out of said concentration column while accumulating the components within said concentration column resulting in concentration of said adsorbable components,
   e. communicating said concentration column with said separation column, and feeding an eluting solution to said concentration column through said switch means,
   f. passing the accumulated components flowing out of said concentration column to said separation column,
   g. interrupting the communication of said concentration column with said separation column, and feeding said eluting solution to said separation column,
   h. separating the components from one another, and
   i. detecting the components, steps (h) and (i) being accomplished simultaneously with steps (a), (b), (c) and (d).

8. Apparatus comprising a packed concentration column capable of accumulating adsorbable components contained in a dilute sample solution by passing the dilute sample solution therethrough in advance, the concentration column containing an adsorbent capable of adsorbing said adsorbable components in narrow bands, the concentration column having an adsorbent encasing section provided with means for connecting at least one lid to the encasing section, filter means provided at both ends of the encasing section, said at least one lid containing a liquid passage passing through the lid from an external lid surface to an internal lid surface adjacent a said filter, the encasing section and the lid being detachable from the apparatus while the encasing section and the lid are connected to one another, holding means detachably mounting said concentration column so that said concentration column can accumulate adsorbable components at a location remote from said apparatus and then be mounted on said holding means, wherein said holding means detachably mounts said concentration column by pressing said concentration column at opposite ends thereof against a resilient means of said holding means, said holding means defining an open side for facilitating insertion and withdrawal of said concentration column therefrom, and means for feeding a desorbing solution to said concentration column in an amount smaller than the amount of sample fed to said concentration column, a separation column for separating the components desorbed by said desorbing solution from one another, valve means for maintaining a communication of said concentration column with said separation column while feeding said desorbing solution to said concentration column, and connecting said concentration column to a discharge outlet for external discharge of a solvent after the feeding of said desorbing solution is completed, means for feeding an eluting solution different from said desorbing solution to said separation column without passing through said concentration column, and means for detecting the components flowing out of said separation column.

9. Apparatus according to claim 8, wherein a means for feeding the dilute sample solution and for feeding the desorbing solution to said concentration column is provided.

10. Apparatus comprising a concentration column having an adsorbent-encasing section provided with screw grooves on its outside surface, at least one lid screw-connectable to the encasing section, and filters provided at both ends of the encasing section, an adsorbent being filled in the encasing section, a liquid passage formed in the lid and passing through the lid from an external lid surface to an internal lid surface adjacent a filter, the encasing section and the lid being detachable from the apparatus while the encasing section and the lid are connected to each other, and adsorbable components being retainable in narrow bands in the adsorbent in the concentration column when the concentration column is disengaged from the apparatus, feeding means for feeding an eluting solution for desorbing the adsorbable components to said concentration column after said concentration column is engaged in the apparatus, a separation column for separating the components passing out of said concentration column from one another, a passage switch means for communicating said concentration column with said separation column while the eluting solution containing the adsorbable components from said concentration column is led to said separation column, and communicating another passage for feeding an eluting solution for separating the adsorbable components to said separation column after the feeding of the eluting solution containing the adsorbable components is completed, means for holding said concentration column between the means for feeding the eluting solution for the desorbing and said switch means, wherein said holding means detachably mounts said concentration column by pressing said concentration column at opposite ends thereof against a resilient means of said holding means, said holding means defining an open side for facilitating insertion and withdrawal of said concentration column therefrom, a passage having an opening provided on said means for holding the concentration column wherein an end of the passage having the opening is in contact with an open end of the lid when said concentration column is inserted into the apparatus, and means for detecting the components flowing out of said separation column.

11. A liquid chromatography process for detecting the presence of a plurality of different adsorbable components in a dilute sample solution containing said adsorbable components comprising passing said sample through a concentration column containing an adsorbent for said adsorbable components so that said adsorbable components are adsorbed by said adsorbent, passing a desorbing solution capable of desorbing said adsorbable components from said adsorbent through said concentration column to produce a desorbed solution of said adsorbable components, passing all of said desorbed solution through a separation column containing an adsorbent for said adsorbable components so that said adsorbable components are retained by said separation column, passing an eluting solution through said separation column to produce an effluent containing said adsorbable components, and detecting the presence of said adsorbable components in said effluent, the amount of said desorbing solution fed to said concentration column being less than the amount of sample solution fed to said concentration column so that said desorbed solution contains said adsorbable components in higher concentration that the concentration of adsorbable components in said sample solution.

12. The process of claim 11, wherein said adsorbable components are nonionic.

13. The process of claim 12, wherein the adsorbent in said concentration column and the adsorbent in said separation column are organic porous adsorbents, said sample solution being a solution of said adsorbable components in a solvent therefor having a high polarity.

14. The process of claim 13, wherein said organic porous adsorbent is a styrene-divinylbenzene copolymer.

15. The process of claim 12, wherein the adsorbent in said concentration column and the adsorbent in said separation column are activated carbon.

16. The process of claim 13, wherein the concentration column is desorbed by a solvent having a low polarity.

17. The process of claim 16, wherein said solvent having a low polarity is selected from the group consisting of ethyl ether, n-hexane, isopropyl alcohol and an aqueous solution containing lithium chloride and methanol.

18. The process of claim 17, wherein said separation column is eluted with an eluting solution selected from the group consisting of methanol, a mixed solution of n-hexane and methanol, and a mixed solution of water and methanol.

19. The process of claim 16, wherein said desorbing solution has a lower polarity than said eluting solution.

20. The process of claim 12, wherein the adsorbent in said concentration column has the same composition as the adsorbent in said separation column.

21. The process of claim 20, wherein the particle size of the adsorbent in said concentration column is larger than the particle size of the adsorbent in said separation column.

22. The process of claim 11, wherein said adsorbable components are ionic.

23. The process of claim 22, wherein the adsorbent in said concentration column and the adsorbent in said separation column are independently selected from ion exchange resins and chelate resins.

24. The process of claim 23, wherein said desorbing solution is the same as said eluting solution.

25. The process of claim 24, wherein the particle size of the adsorbent in said concentration column is larger than the particle size of the adsorbent in said separation column.

26. The process of claim 25, wherein the adsorbent in said concentration column has the same composition as the adsorbent in said separation column.

27. The process of claim 23, wherein the particle size of the absorbent in said concentration column is larger than the particle size of the adsorbent in said separation column.

28. The process of claim 23, wherein the adsorbent in said concentration column has the same compositions as the adsorbent in said separation column.

29. The process of claim 11, wherein a plurality of different samples are to be successively analyzed, the adsorbable components in one of said samples being separated from one another in said separation column while the adsorbable components in another sample are being adsorbed by said concentration column.

30. The process of claim 11, wherein a plurality of different samples are to be successivley analyzed, said plurality of different samples being recovered from a first location remote from a second location at which separation of said adsorbable components from one another is to occur, said plurality of different samples being passed through a plurality of different concentration columns, one concentration column for each sample, said plurality of concentration columns being transported from said first location to said second location, and said plurality of concentration columns being successivley attached to said separation column so that the adsorbable components in each individual sample can be separated from one another and detected.

31. Apparatus for carrying out a liquid chromatography process on a dilute sample solution containing a plurality of adsorbable components therein, said apparatus comprising a concentration column containing an adsorbent for said adsorbable components, said concentration column having an adsorbent-encasing section provided with screw grooves on its outside surface, at least one lid screw-connectable to the encasing section, and filters provided at both ends of the encasing section, an adsorbent being filled in the encasing section, a liquid passage formed in the lid and passing through the lid from an external lid surface to an internal lid surface adjacent a filter, the encasing section and the lid being detachable from the apparatus while the encasing section and the lid are connected to each other, and adsorbable components being retainable in narrow bands in the adsorbent in the concentration column when the concentration column is disengaged from the apparatus, holding means detachably mounting said concentration column so that said concentration column can accumulate adsorbable components at a location remote from said apparatus and then be mounted on said holding means, wherein said holding means detachably mounts said concentration column by pressing said concentration column at opposite ends thereof against a resilient means of said holding means said holding means defining an open side for facilitating insertion and withdrawal of said concentration column therefrom, first feeding means for feeding said sample solution in a predetermined amount to said concentration column, second feeding means for feeding a desorbing solution to said concentration column in an amount less than said predetermined amount, a separation column containing an adsorbent for said adsorbable components, valve means for maintaining a communication of said concentration column with said separation column while said desorbing solution is fed to said concentration column, and connecting said concentration column to a discharge outlet for external discharge of a solvent after the feeding of said desorbing solution is completed, a third feeding means for feeding an eluting solution to said separation column different from said desorbing solution without passing through said concentration column after the desorbing solution flowing out of said concentration column is led to said separation column, and means for detecting the adsorbable components passing out of said separation column.

32. A chromatographic apparatus comprising:

a concentration column having an adsorbent-encasing section provided with screw grooves on its outside surface, at least one lid screw-connectable to the encasing section, and filters provided at both ends of the encasing section, the encasing section filled with an adsorbent, and a liquid passage formed in the lid and passing through the lid from an external lid surface to an internal lid surface adjacent a filter, the encasing section and the lid being detachable from the apparatus while the encasing section and the lid are connected to each other, an accumulation of adsorbed components in the concentration column resulting from passage of a predetermined amount of a dilute sample solution containing adsorbable components through the concentration column in advance;

holding means detachably mounting said concentration column so that said concentration column can accumulate adsorbable components at a location remote from said apparatus and then be mounted on said holding means wherein said holding means detachably mounts said concentration column by pressing said concentration column at opposite ends thereof against a resilient means of said holding means, said holding means defining an open side for facilitating insertion and withdrawal of said concentration column therefrom;

feeding means for feedng a smaller volume of a desorbing solution than that of said sample solution to said concentration column after said concentration column is engaged in said holding means;

a separation column for separating components passing out of said concentration column from one another;

means for feeding an eluting solution to said separation column;

valve means for maintaining a communication of said concentration column with said separation column while the desorbing solution containing the adsorbable components flows out of said concentraion column, and communicating said means for feeding the eluting solution with said separation column after the flowing of the desorbing solution from said concentration column is completed; and means for detecting the components flowing out of said separation column, the apparatus being free from a means for feeding the sample solution to said concentration column.

33. Apparatus according to claim 32, wherein said concentration column has projected parts at said opposite ends, said holding means having taper surfaces capable of guiding said projected parts during insertion of said concentration column in said holding means.

34. Apparatus according to claim 32, wherein a pair of passage switch means are provided in an interlocked manner at both inlet and outlet sides of the means for holding the column.

35. Apparatus according to claim 34, wherein a plurality of concentration columns are arranged in parallel with respect to said feeding means and with respect to said separation column, said pair of passage switch means selectively placing only one concentration column in fluid communication with said feeding means and said separation column at any one time.

36. A liquid chromatography process comprising:

feeding a predetermined amount of a sample solution having adsorbable components therein to a concentration column capable of producing a solution of said adsorbable components in higher concentration than the concentration of the adsorbable components in the sample solution to be measured;

interrupting a communication of the concentration column with a separation column while feeding said sample solution to the concentration column, and discharging an effluent from the concentration column thereby accumulating the adsorbable components in said concentration column;

communicating said concentration column with said separation column, and feeding a desorbing solution for desorbing the adsorbable components accumulated in said concentration column into said concentration column, an amount of the desorbing solution being smaller than said predetermined amount of said sample solution;

directing the desorbing solution flowing out of said concentration column to said separation column;

separating the components from one another with an eluting solution fed to said separation column; and detecting the components contained in an effluent from said separation column.

* * * * *